United States Patent [19]

Maggioni

[11] 4,183,861

[45] Jan. 15, 1980

[54] PROCESS FOR PREPARING AROMATIC METHYLENE-DIOXY COMPOUNDS

[75] Inventor: Paolo Maggioni, Cernusco Montecchia, Italy

[73] Assignee: Brichima S.p.A., Milan, Italy

[21] Appl. No.: 764,424

[22] Filed: Jan. 31, 1977

[30] Foreign Application Priority Data

Jan. 30, 1976 [IT] Italy .............................. 19735 A/76

[51] Int. Cl.$^2$ .......................................... C07D 317/44
[52] U.S. Cl. ............................................. 260/340.5 R
[58] Field of Search ................................ 260/340.5 R

[56] References Cited

U.S. PATENT DOCUMENTS

| | | | |
|---|---|---|---|
| 3,726,924 | 4/1973 | Leimgruber et al. | 260/340.5 X |
| 3,838,051 | 9/1974 | Andress | 260/340.5 X |

Primary Examiner—Ethel G. Love

Attorney, Agent, or Firm—Joseph W. Molasky

[57] ABSTRACT

A method for preparing aromatic methylenedioxybenzene products which are optionally substituted in the aromatic ring by alkyl, aldehydo, carboxy, alkoxy, halo or nitro moieties; which comprises treating the corresponding dihydroxybenzene with methylene chloride in the presence of a catalyst selected from among ammonium, phosphonium or arsonium chlorides and bromides. The reaction is conducted in the aqueous phase in the presence of a suitable base, such as a sodium derivative to form a sodium salt of the dihydroxybenzene reactant.

The aromatic methylenedioxy products of this invention are known compounds which are used in the chemical, pharmaceutical and cosmetic industries and they have utility as intermediates in the preparation of other known compounds.

10 Claims, No Drawings

PROCESS FOR PREPARING AROMATIC METHYLENE-DIOXY COMPOUNDS

This invention relates to a novel method for preparing aromatic methylenedioxy products via the methylenation of aromatic ortho-dihydroxy compounds.

The products of this process are widely used in the chemical industry and particularly in the pharmaceutical and cosmetic industries. Typical of the products obtained by the present method are, for example, oxalinic acid and piperonal.

BACKGROUND

There are several known methods for preparing aromatic methylenedioxy products including the methylenation of the corresponding ortho-dihydroxy precursors. However, all of the known processes suffer from one or more of the following disadvantages:

(a) They employ costly methylenation agents such as bromine and iodine derivatives;

(b) Dilute aqueous solutions are required to assure intramolecural cyclization and preclude the intermolecular reaction which generally results in the formation of dimers and polymers. And, when the aqueous solutions are too dilute there is the problem of low yield and the separation of the mother liquors and recovery of same, and these additional steps make the process uneconomical;

(c) Dipolar aprotic solvents such as dimethylsulphoxide and dimethylformamide under anhydrous donditions are employed; and although these solvents afford good yields of the dioxymethylene product and good reaction speeds are obtained, the consumption and recovery of costly solvents renders the process uneconomical.

We have now discovered a new method for the preparation of methylenedioxybenzene products which overcomes the aforementioned difficulties

THE INVENTION

This invention consists essentially of a novel method for preparing methylenedixoybenzene products of the following formula:

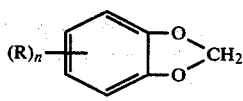

I wherein R is hydrogen; lower alkyl of 1–4 carbon atoms such as methyl, ethyl, n-propyl or n-butyl and the like; aldehydo; carboxy; alkoxy of 1–4 carbon atoms such as methoxy, ethoxy, n-propoxy or n-butoxy and the like; halo such as chloro, bromo or iodo and the like; or nitro; and n is an integer having a value of 1–3. These products (I) are obtained by treating a compound of the formula:

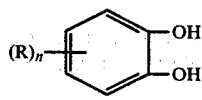

wherein R and n are as defined above, with methylene chloride in the presence of a catalyst selected from the group consisting of ammonium, phosphonium and arsonium salts.

The ammonium salts which are suitable for use in the process of this invention are compounds of the formula:

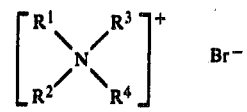

in which $R^1$, $R^2$, $R^3$ and $R^4$ are the same or different alkyl radicals containing from 2–8 carbon atoms such as ethyl, n-propyl, n-butyl, pentyl, hexyl, heptyl or octyl and the like.

Other ammonium salts which are suitable for use as catalysts in the process of this invention are compounds of the formula:

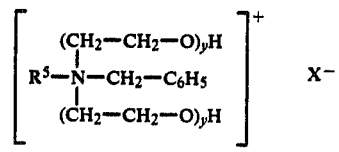

wherein $R^5$ is alkyl of 10–20 carbon atoms such as decyl, undecyl, dodecyl, octadecyl, nonadecyl or eicosyl and the like; and $X^-$ is a chloro or bromo cation; y is an integer having a value of 1–12; and $—C_6H_5$ is phenyl.

The phosphonium and arsonium salts which can be used as catalysts in the present invention are those of the formula:

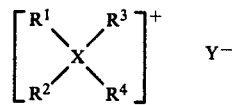

wherein X is the phosphonium anion (P) or the arsonium anion (As); and $R^1$, $R^2$, $R^3$ and $R^4$ are the same or different linear alkyl radicals having from 2–8 carbon atoms such as ethyl, n-propyl, n-butyl, pentyl, heptyl or octyl and the like and $Y^-$ is a chloro or bromo cation.

A preferred embodiment of this invention relates to the preparation of methylenedioxybenzenes of the following formula:

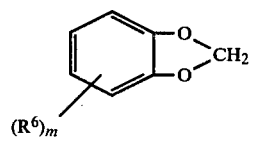

II wherein $R^6$ is hydrogen, lower alkyl such as methyl, ethyl and the like, aldehydo (ie., —CHO) or carboxy; and m is an integer having a value of 1–2; which comprises treating a dihydroxybenzene of the formula:

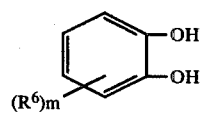

wherein R[6] and m are as defined above, with methylene chloride in the presence of a catalyst selected among ammonium, phosphonium and arsonium chlorides and bromides.

Other quaternary ammonium, phosphonium and arsonium salts also exert a catalytic action on the process of this invention, but only the aforementioned catalysts result in a useful industrial process. Other quaternary salts afford good yields only if used with methylene bromide; however, this is uneconomical because methylene bromide is an industrially expensive product.

Thus, the method of this invention has particular application to industrial processes and constitutes a considerable improvement over known processes.

It is critical of this invention that only methylene chloride and the designated class of catalysts by utilized. The reaction will not occur at all in the absence of catalysts chosen from the group consisting of quaternary ammonium, phosphonium and arsonium salts.

Likewise, the reaction will not take place in the presence of ammonium, phosphonium or arsonium iodides.

In practice, the process of this invention is effected by subjecting a mixture of methylene chloride, an aqueous concentrated solution of the sodium salt of the ortho-dihydroxybenzene derivative and small quantities of catalyst to fierce agitation.

Alternatively, the solid or aqueous sodium hydrate and the ortho-dihydroxybenzene reactant, either as such or in aqueous solution, may be added at the same time or successively, to a solution of the catalyst in methylene chloride.

As the reaction products form they are extracted by the methylene chloride, and upon completion of the reaction it is possible to obtain a simple and rapid separation of the reaction product from the starting compounds by simply decanting the organic layer. The starting materials remain, essentially, in the aqueous layer.

In separating out the reaction products, the methylene chloride is first distilled from the organic phase and recycled, and then the methylenedioxy product is distilled off at high purity. The catalyst remains as a residue and can be recovered and recycled.

The quantity of methylene chloride employed in this method may vary from between about 1 and 5 moles per mole of the ortho-dihydroxybenzene reactant. However, it is always advantageous to operate with an excess of methylene chloride so as to afford a double phase and extract the product in the organic phase.

The catalysts of this invention are used in quantities of from about 1 to 10 molar percent with respect to the ortho-dihydroxybenzene reactant and they may be recycled.

The amount of caustic soda employed is between about 30 and 150% of equivalents with respect to the ortho-dihydroxybenzene reactant.

The concentration of the disodium salt of the ortho-dihyroxybenzene reactant in the aqueous phase must be kept between 0.1 and 40% by weight.

The reaction occurs between 30° and 120° C., but maximum reaction speed is obtained between 60° and 90° C.

This invention will now be described by reference to specific embodiments. However, it is to be understood that these embodiments are illustrative only and are not limitative. Therefore, any substitution of equivalent materials or modification in the reaction conditions is considered as being within the scope of this invention and not a departure therefrom.

EMBODIMENTS

The process will be evident from the following Examples:

EXAMPLE 1: METHYLENEDIOXYBENZENE:

Methylene chloride (100 ml., 1.56 moles), tetrabutylammonium bromide (6.42 g., 0.02 moles) and water (200 ml.) are placed in an autoclave. To this mixture is added a total of 15 g. pyrocatechin (0.1362 moles) and sodium hydroxide (15.9 g., 0.3975 moles) in flake form in successive stages.

The reaction temperature is maintained at 70° C. and the pressure within the autoclave rises to a maximum of 2.4 atmospheres. The reaction is completed within three hours.

After the reaction is completed, the organic phase is separated and excess methylene chloride is distilled off and recycled. Pure methylenedioxybenzene (13.8 g.; 83% yield) is obtained by distillation.

Tetrabutylammonium bromide remains as a distillation residue and this material can be recovered and reused as a catalyst to produce additional product.

By substituting pyrocatechoic acid (ie., 2,3-dihydroxybenzoic acid) for the pyrocatechin of Example 1, and otherwise following the procedure described therein, the product 1-carboxy-methylenedioxybenzene is obtained.

EXAMPLE 2: METHYLENEDIOXYBENZENE:

By following the procedure described in Example 1, but substituting hexadecyltributyl phosphonium bromide for tetrabutylammonium bromide in an otherwise analogous process, 11.65 g. of methylenedioxybenzene (70% yield) is obtained.

EXAMPLE 3: 1-METHYL-3,4-METHYLENEDIOXYBENZENE:

Methylene chloride (1.56 g., 100 ml.) and tetrabutylammonium bromide (6.42 g., 0.02 moles) are placed in an autoclave, and to this mixture is added a total of 24.8 g. of 4-methylpyrocatechin (0.2 moles) and caustic soda (24 g., 0.6 moles) in flake form, with agitation, at 80° C. The reaction is completed within five hours.

After the reaction is completed, the product is recovered by following the procedure described in Example 1, that is, the organic phase is separated, excess methylene chloride is distilled off and recycled and 1-methyl-3,4-methylenedioxybenzene (19.4 g.; 71.3% yield) is obtained by distillation.

EXAMPLE 4: PIPERONAL:

Methylene chloride (100 ml., 1.56 moles), tetrabutylammonium bromide (6.42 g., 0.02 moles) and water (200 ml.) are placed in an autoclave. A total of 27.6 g. of protocatechic aldehyde (0.2 moles) and caustic soda (24 g., 0.6 moles) in water (20 ml.) are then added to the autoclave in stages at a temperature of 70° C.

The pressure within the autoclave increases to a maximum of 2.4 atmospheres and the reaction is completed within four hours.

The reaction mixture is allowed to cool to ambient temperatures and the organic phase is separated. Excess methylene chloride is recovered from the organic phase by distillation and high purity piperonal (21 g., 70% yield) is isolated. The product is identified by gas chromatography and infra-red spectrum analysis by comparing against a pure sample.

Upon substituting tetramethylarsonium chloride, for the tetrabutylammonium bromide of Example 4, and otherwise following the procedure described therein, an identical piperonal product is obtained.

What is claimed is:

1. A method for preparing a compound of the formula:

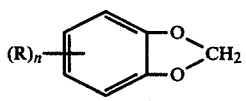

wherein R is hydrogen, alkyl of 1-4 carbon atoms, aldehydo, carboxy, alkoxy of 1-4 cations, halo or nitro; and n is an integer having a value of 1-3 which comprises treating a compount of the formula:

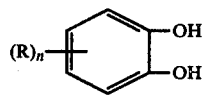

wherein R and n are as defined above, with methylene chloride, in the presence of a catalyst selected from among ammonium, phosphonium, or arsonium salts.

2. A method for preparing a compound of the formula:

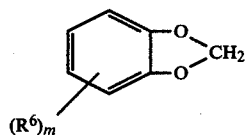

wherein $R^6$ is hydrogen or lower alkyl and m is an integer having a value of 1-2; which comprises treating a compound of the formula:

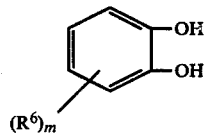

wherein R and m are as defined above, with methylene chloride in the presence of an ammonium or phosphonium salt.

3. The method of claim 2 wherein $R^6$ is hydrogen.

4. The method of claim 2 wherein $R^6$ is methyl and m is an integer having a value of 1-2.

5. The method of claim 1 wherein the catalyst is selected from the group consisting of:

(a) a quaternary ammonium salt of the formula:

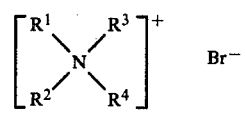

in which $R^1$, $R^2$, $R^3$ and $R^4$ are the same or different alkyl moieties of 2 to 8 carbon atoms;

(b) a quaternary ammonium salt of the formula:

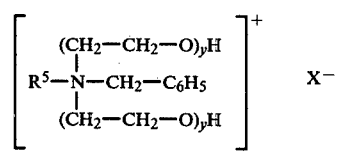

in which $R^5$ is alkyl of 10 to 20 carbon atoms, y is an integer of 1 to 12 and $X^-$ is a chloro or bromo cation;

(c) a quaternary phosphonium or arsonium salt of the formula:

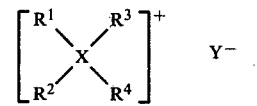

in which X is the phosphonium or arsonium anion, $R^1$, $R^2$, $R^3$ and $R^4$ are the same or different linear alkyl radicals of 2 to 18 C atoms and $Y^-$ is a chloro or bromo cation.

6. The method of claim 1 wherein the ratio of the reactants is 1 to 5 moles of methylene chloride per mole of aromatic ortho-dihydroxy compound.

7. The method of claim 1 wherein the catalyst is present in the amount of 1 to 10 molar % with respect to the aromatic dihydroxy compound.

8. The method of claim 1 wherein the concentration of the aromatic orthodihydroxy compound in the aqueous phase is kept between about 0.1 and 40% by weight.

9. The method of claim 1 which is effected at a temperature between about 30° and 120° C.

10. The method of claim 1 which is effected at a temperature between about 60° and 90° C.

* * * * *